(12) United States Patent  
Sullivan et al.

(10) Patent No.: US 7,112,416 B2
(45) Date of Patent: Sep. 26, 2006

(54) DETECTION OF MICROBIOLOGICAL GROWTH IN A SEALED CONTAINER USING A POISING AGENT

(76) Inventors: Nadine Michele Sullivan, 569 Heather Stone Ridge, Sun Prairie, WI (US) 53590; Sara Elizabeth Allen, 312 Main St., Sun Prairie, WI (US) 53590

( * ) Notice: Subject to any disclaimer, the term of this patent is extended or adjusted under 35 U.S.C. 154(b) by 229 days.

(21) Appl. No.: 10/665,105

(22) Filed: Sep. 17, 2003

(65) Prior Publication Data

US 2005/0058986 A1 Mar. 17, 2005

(51) Int. Cl.
*C12Q 1/04* (2006.01)
*C12Q 1/06* (2006.01)

(52) U.S. Cl. .......................................... 435/34; 435/39
(58) Field of Classification Search ...................... None
See application file for complete search history.

(56) References Cited

U.S. PATENT DOCUMENTS

| | | |
|---|---|---|
| 3,743,581 A | 7/1973 | Cady et al. |
| 3,907,646 A | 9/1975 | Wilkins et al. |
| 4,152,213 A | 5/1979 | Ahnell |
| 5,232,839 A | 8/1993 | Eden et al. |
| 5,501,959 A | 3/1996 | Lancaster et al. |
| 6,395,506 B1 | 5/2002 | Pitner et al. |

*Primary Examiner*—Sandra E. Saucier
(74) *Attorney, Agent, or Firm*—Howard M. Cohn

(57) ABSTRACT

According to the present invention, there is disclosed a method of stabilizing the output signal of a system that detects microbiological growth in a sealed sample container that contains a sample which may contain an unknown microorganism. One embodiment relates to a method of providing a sealed sample container which contains a fluid mixture of a culture broth, the sample, and at least one poising agent for stabilizing the base line pressure within a headspace above the fluid mixture in the sample container. By monitoring pressure changes within the headspace of the sealed sample container, the presence of microbiological growth within the sealed sample container as a function of the change of the pressure in the headspace is indicated.

12 Claims, 4 Drawing Sheets

DETECTION OF MICROBIOLOGICAL GROWTH IN A SEALED CONTAINER USING A POISING AGENT

TECHNICAL FIELD OF THE INVENTION

The present invention relates an improved method of detecting microbiological growth and, more particularly, to a method of filtering background noise of chemical redox reactions to prevent or minimize false positives in analyzing a sample using the technique of measuring the redox reactions in a sealed container which is a result of microbial growth.

BACKGROUND OF THE INVENTION

Current methods are manual for detection of microorganisms. In such manual systems, a sample of material to be tested is incubated, usually in a suitable growth medium. Various manipulations such as agitation are required during the incubation and monitoring period. The detection of growth is achieved by visual inspection. For example, technicians observe and assess the growth of bacteria on a Petri dish, or evaluate the clarity of a broth (turbidity). The visual observations and assessments are subjective and, therefore, subject to error. In addition, these manual methods are labor intensive, require significant manipulation, and entail observation of all samples by laboratory personnel.

A number of methods have been suggested to detect the presence or absence of microorganisms by less subjective means. U.S. Pat. No. 3,743,581 (1973), Cady et al., discloses a method for monitoring microbiological growth by measuring the change in the conductivity of selected nutrient media inoculated with a sample.

U.S. Pat. No. 3,907,646 (1975), Wilkins et al, describes measurement of gas production of microorganisms. A pressure transducer is applied to a test tube and connected to a power source and strip recorders. Measurements are recorded on the strip recorders producing a plot of an electrical signal, which is generated over time, indicative of the presence and quantity of microorganisms. The instrument is very large and cumbersome, making it impractical to monitor multiple samples.

U.S. Pat. No. 4,152,213 describes a system by which the growth of microorganisms in a sealed container is detected by measuring reduction in headspace pressure as the microorganism consumes oxygen and comparing the reduction in pressure to a reference standard of the initial pressure. A vacuum sensor senses a reduction in pressure in the headspace of a container and provides an electrical signal to remote electronics. A major problem with such a system is that it is limited to those organisms that consume oxygen. Many microorganisms do not consume oxygen. Thus, the presence of a vacuum is not a universal indicator of microbial growth. Another problem with such a system is that in many instances the maximum decrease in the headspace pressure is small in comparison to the natural variations of the atmospheric pressure. In addition, this method requires precise pressure sensors since it functions on the basis of absolute value of initial and threshold pressures.

U.S. Pat. No. 5,232,839 describes a system by which the presence of microbiological growth in a sealed sample container is detected by measuring the rate of change of headspace pressure in the container as the microorganism consumes oxygen and comparing the change in pressure to a reference standard of the initial pressure. A vacuum sensor senses a reduction in pressure in the headspace of a container and provides an electrical signal to remote electronics. A major problem exists for weak consumers, or slower growing organisms, where background redox reactions can occur because the reagents added to the culture broth cause an unpredictable change in the pressure differential in the headspace due to reduction oxidation. A major problem with such a system is that it suffers from false positives due to background redox reactions.

It is well known that pH buffers are utilized for end point growth determinations using pH dyes, such as phenol red. The pH buffers are known to stabilize background pH drift due to chemical reactions within the test system. It is with this concept that one uses Redox buffer/dye systems to stabilize background chemical redox reactions, which can be applied generally to a detection system for microbial growth.

Use of poising agents to stabilize redox dyes for determination of end point growth reactions, such as antibiotic susceptibility has been described in U.S. Pat. No. 5,501,959 by Lancaster et al.

U.S. Pat. No. 6,395,506 discloses a device for monitoring cells for detection and evaluation of metabolic activity of eukaryotic and/or prokaryotic cells based upon their ability to consume dissolved oxygen. The methods utilize a luminescence detection system which makes use of the sensitivity of the luminescent emission of certain compounds to the presence of oxygen, which quenches (diminishes) the compound's luminescent emission in a concentration dependent manner.

SUMMARY OF THE INVENTION

According to the present invention, there is disclosed a method of stabilizing the output signal of a system that detects microbiological growth in a sealed sample container that contains a sample which may contain an unknown microorganism. The method comprises: (a) providing a sealed sample container which contains a fluid mixture of a culture broth, at least one reagent mixture, the fluid sample, and at least one poising agent for stabilizing the base line pressure within a headspace above the fluid mixture in the sample container; (b) monitoring pressure changes within the headspace of the sealed sample container; and (c) indicating a presence of microbiological growth within the sealed sample container as a function of the change of the pressure in the headspace.

Also according to the invention, the method includes providing a pair of coupled poising agents. The pair of coupled poising agents are selected from the group consisting essentially of ferricyanide/ferrocyanide and ferrous/ferric.

Further according to the invention, the method includes providing a second poising agent which is a reversible oxidation-reduction indicator. The second poising agent selected from the group consisting essentially of methylene blue, toluidine blue, azure I, and gallocyanine.

Still further according to the present, the method includes providing at least two reagent mixtures. One reagent mixture is a growth supplement and a second reagent mixture of an antibiotic supplement.

According to another embodiment of the invention, there is also disclosed a method of stabilizing the output signal of a system that is monitoring a liquid mixture in a sealed container with a sensor that detects redox outputs related to microbial growth. The method comprises the step of mixing into the liquid mixture at least one poising agent for stabilizing the "output" of the test within the sample container.

Also according to another embodiment of the invention, the step of mixing at least one poising agent comprises the step of mixing a pair of coupled poising agents. The pair of coupled poising agents are selected from the group consisting of ferricyanide/ferrocyanide and ferrous/ferric.

Further according to another embodiment of the invention, a second poising agent which is a reversible oxidation-reduction indicator can be mixed into the liquid mixture. The second poising agent is selected from the group consisting essentially of methylene blue, toluidine blue, azure I, and gallocyanide.

BRIEF DESCRIPTION OF THE DRAWINGS

Reference will be made in detail to preferred embodiments of the invention, examples of which are illustrated in the accompanying drawings. The drawings are intended to be illustrative, not limiting. Although the invention will be described in the context of these preferred embodiments, it should be understood that it is not intended to limit the spirit and scope of the invention to these particular embodiments.

Certain elements in selected ones of the drawings may be illustrated not-to-scale, for illustrative clarity.

Figure 1:
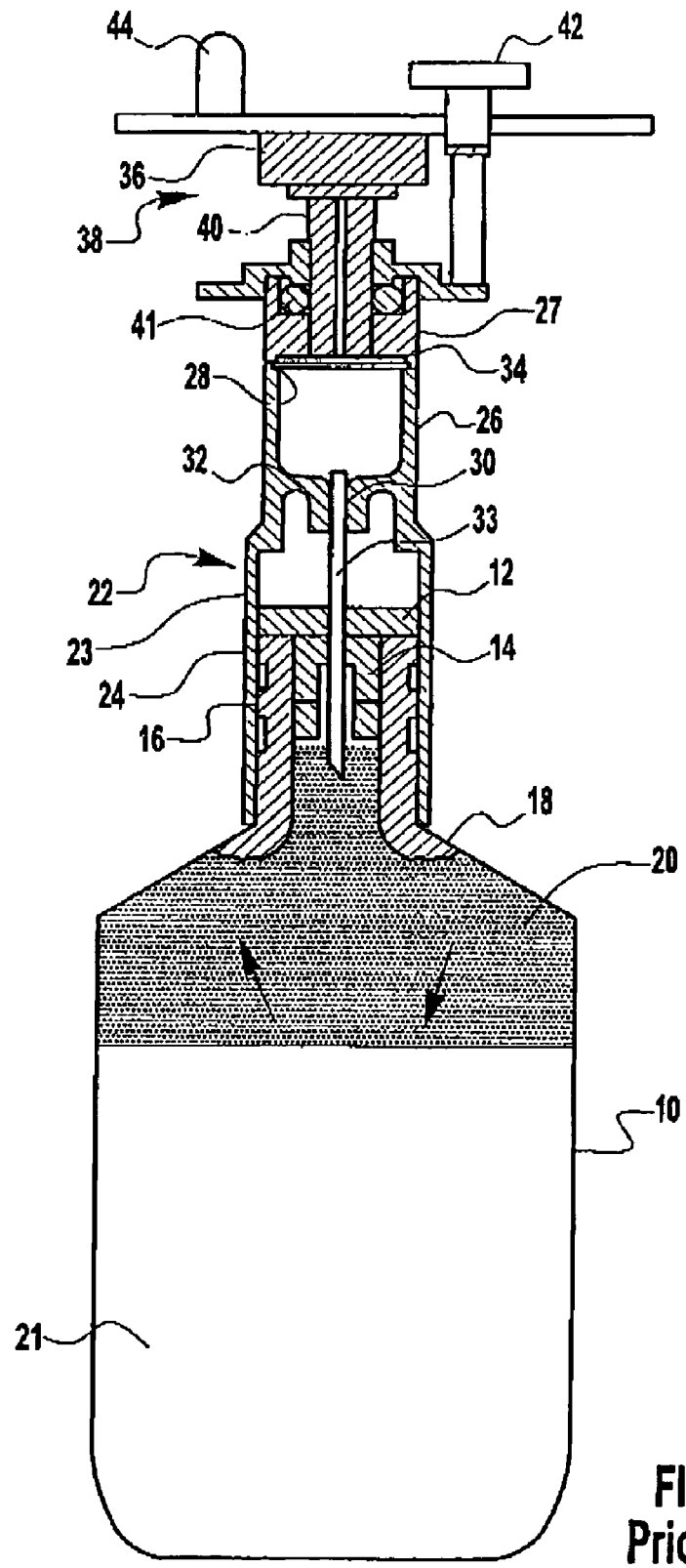
Figure 3:
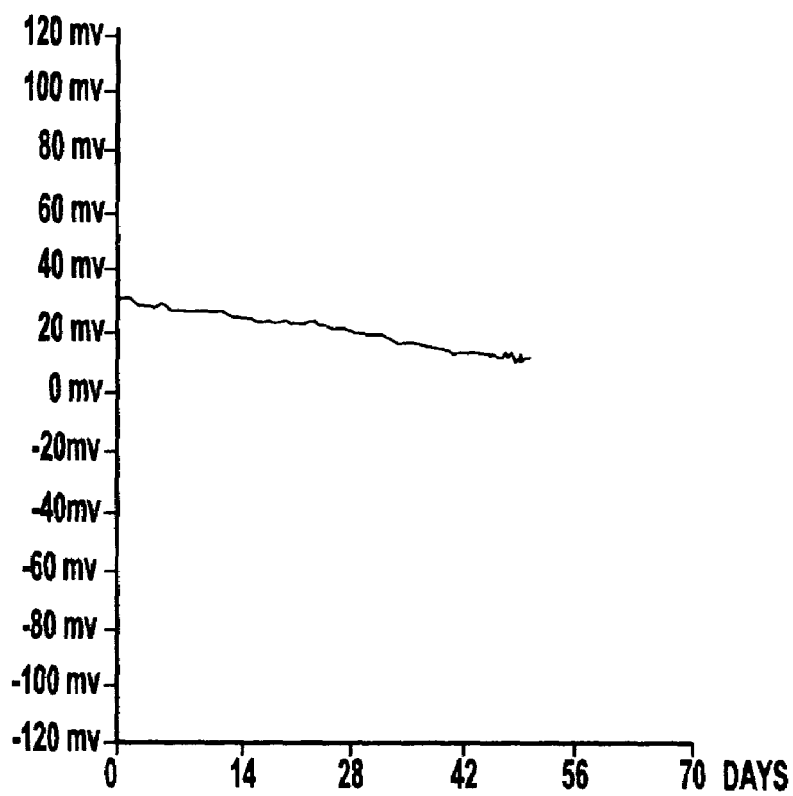
Figure 2:
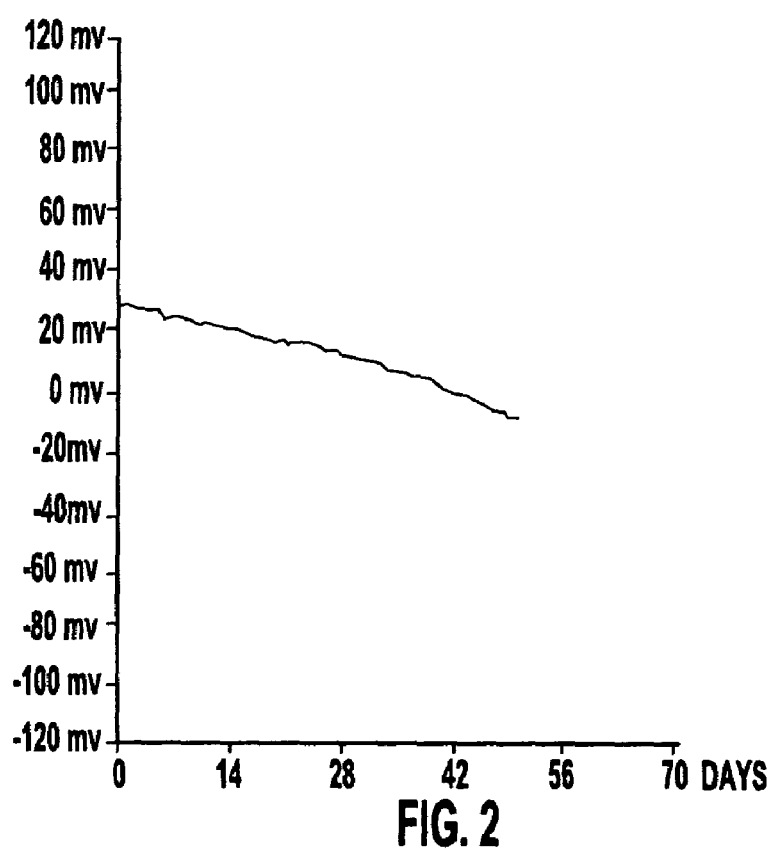
Figure 4:
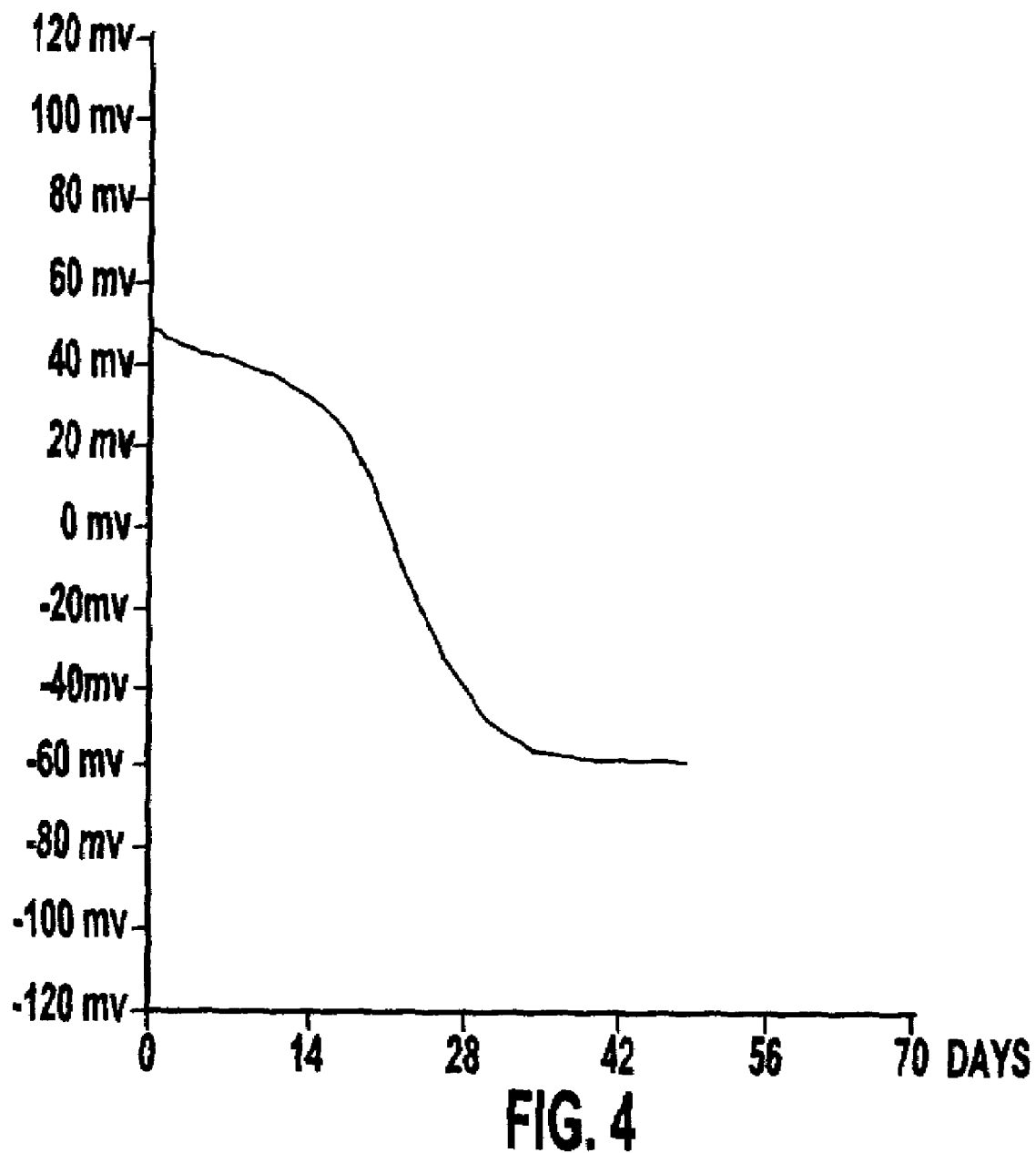
Figure 5:
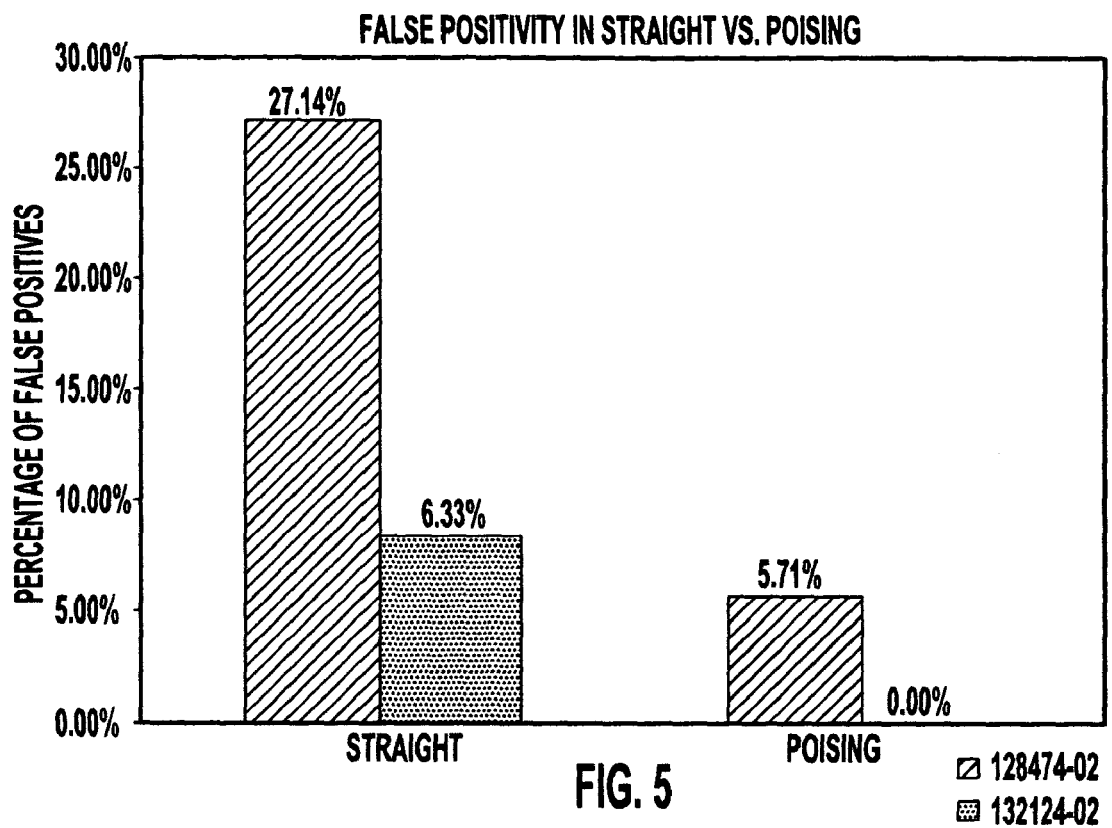
Figure 6:
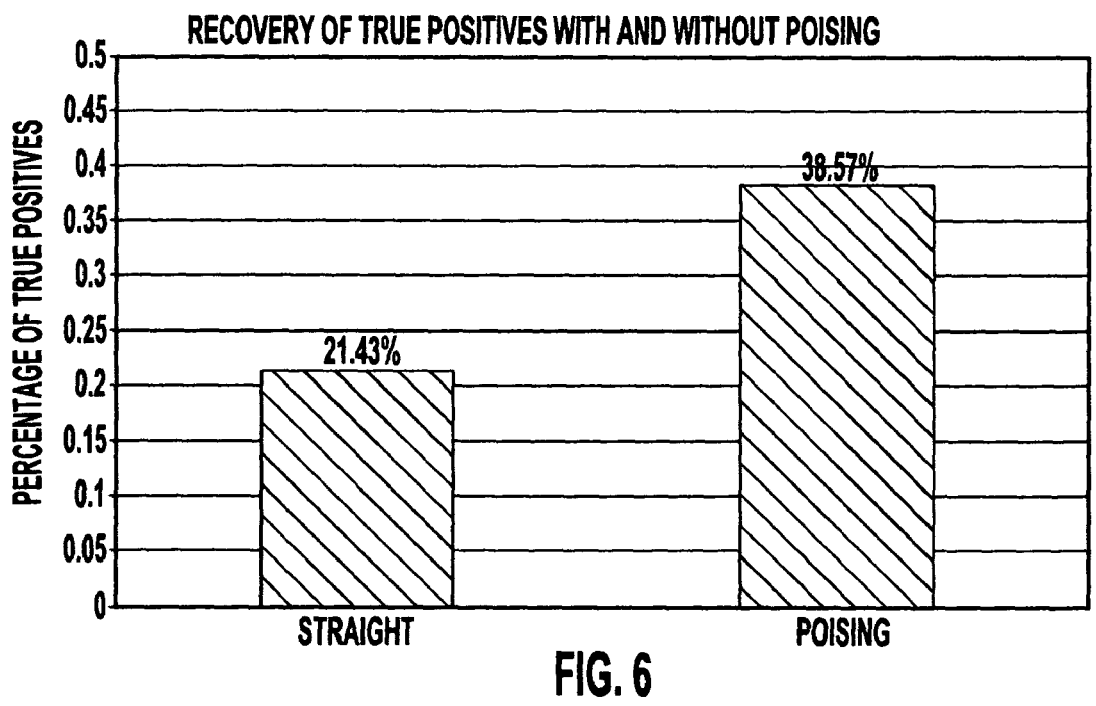

The structure, operation, and advantages of the present preferred embodiment of the invention will become further apparent upon consideration of the following description taken in conjunction with the accompanying drawings, wherein:

FIG. 1 is an elevational view of a prior art culture container and pressure sensing device connected to the bottle headspace by a disposable connector adapted to be used in performing the method of the present invention;

FIG. 2 is a graph showing the curve of voltage versus time in a pressure analysis of a typical mixture of a culture broth and reagents;

FIG. 3 is a graph showing the curve of voltage versus time in a pressure analysis of the identical mixture of culture broth and reagents as shown in the curve of FIG. 2 plus a pair of poising agents added to the mixture in accordance with the present invention;

FIG. 4 is a graph showing the curve of voltage versus time in a typical pressure analysis of a mixture of culture broth and reagents as shown in the curve of FIG. 2 plus a pair of poising agents added to the mixture in accordance with the present invention, plus a test sample containing a microorganism for a positive growth response;

FIG. 5 is a graph showing percentage of false positivity using the prior art mixture of culture broth and reagents as compared to the mixture of culture broth and reagents and poising agents according to the present invention; and FIG. 6 is a graph showing the percentage of true positives with the prior art mixture of culture broth and reagents as compared to the mixture of culture broth and reagents and poising agents according to the present invention.

DETAILED DESCRIPTION OF THE INVENTION

Referring to FIG. 1, a vial or container 10 of well-known construction such as a glass bottle having a cap 12 with a resilient elastomeric stopper 14 that is exposed at its upper end in the performance of the method. The container 10 is filled with a culture broth of either an aerobic or anaerobic culture medium depending upon the microorganism, which is to be detected prior to sealing the container with cap 12. The container 10 includes a neck 16 and a shoulder 18.

Besides the culture broth, one or two types of a growth supplement, such as OADC (oleic acid, albumin, dextrose and catalase), egg yolk, or any supplement required to enhance growth, can be added to the culture broth in the bottle. The growth supplement is typically added to the culture broth before the bottle is sealed. In addition, an antibiotic supplement, to inhibit microorganisms, other than the target, present within the sample can be added to the culture broth. For example, the culture medium or broth can include naladixic acid, amphoteracin B, vancomycin. Here again, the antibiotic supplement is typically added to the culture broth and possibly the growth supplement before the bottle is sealed. At this stage, in the prior art, it is customary to add the sample to be tested to the bottle. In a typical system, the sample is 0.5% to 5% of the liquid mixture which includes the sample, the culture broth, the growth supplement (if included) and/or the antibiotic supplement (if included). The growth supplement is 1% to 10% of the liquid mixture and the antibiotics (if included) are 0.001% to 0.1%(w/v) of the liquid mixture.

However, in the prior art systems, there was often a problem of false positives due to chemical redox reactions (reduction/oxidation). The reagents themselves, such as the growth supplement and/or the antibiotic supplement can react with oxygen in the headspace or the sensor, even without a sample being added to the mixture in the container 10. Thus, there can be a change in the concentration of oxygen within the system and therefore, the pressure in the headspace 20 above mixture 21 irrespective of the sample. Utilization or consumption of oxygen within the system due to reagent-driven chemical reactions (baseline drift) that will, in turn, cause increased numbers of false positives. This baseline drift, also referred to as background noise, cannot be predicted because the reagents are not chemically defined and are comprised of variable amounts of reactive components.

According to the present invention, a poising agent (a oxidation-reduction [redox] stabilizer) is added to the mixture of the culture broth and the reagents, such as the growth supplement and/or the antibiotic supplement. Surprisingly, it has been found that that one or two poising agents act to stabilize the effects of the reagents, i.e. the growth supplement and/or the antibiotic supplement, and thereby significantly reduce the baseline drift.

Preferably, a pair of coupled poising agents will be added to the growth medium to stabilize the oxidation-reduction potential within the range where the culture broth and reagent mixture is oxidized. Suitable poising pairs include ferricyanide/ferrocyanide, ferrous/ferric, and the like.

Using the ferricyanide/ferrocyanide as the coupled poising agents is preferred. The concentration and ratios of the ferricyanide and ferrocyanide in the culture broth will affect the stability of the reagents and will be selected to control the autoreduction effect.

The ferricyanide/ferrocyanide ratio affects the actual redox potential value and controls the beginning potential. If the initial beginning potential is too high, it creates a large oxidation state that has to be to overcome. This large oxidation state delays or inhibits desired metabolic reduction. If the initial beginning potential is too low, it increases the probability for baseline drift thereby increasing false positives.

The preferred concentration is 0.0001M, with the range of 0.00005M to 0.001M total concentration of both components being useful. The preferred ferricyanide/ferrocyanide ratio is 1:1 with ratios of 1:4 to 4:1 of ferricyanide/ferrocyanide being acceptable.

In addition to the coupled poising agents, the poising agent of the present invention will preferably further include a second poising agent, which is itself a reversible oxidation-reduction indicator. It has been found that methylene blue acts to stabilize the oxidation-reduction potential of the growth medium. Other suitable second poising agents include toluidine blue, azure I, and gallocyaninde.

In operation, the growth supplement and or/the antibiotic supplement and/or the one or two poising agents are added to the culture broth prior to sealing the bottle 10 with the stopper 14. The resulting mixture is mixed by any conventional means. Then, the sample is added to the mixture of the growth supplement and the other reagents and poising agents and the entire mixture is mixed.

The sample can be added through means such as a hypodermic needle (not shown) inserted through the stopper 14. A disposable plastic fitment 22 comprising a sleeve 23 is telescoped over the neck 16 of the container 10 so that the lower end of the sleeve 23 engages the shoulder 18, see FIG. 1. The sleeve 23 includes a lower tubular portion 24 and an integral upper tubular portion 26 that extends upwardly from lower tubular portion 24 and is formed with an opening 28 communicating with the opening 30 of an integral inner tubular projection 32 into which a hypodermic needle 33 is frictionally and sealingly supported, as shown in FIG. 1. A top section 27 of upper tubular projection 26 secures a hydrophobic vent filter or membrane 34 in the opening 28. The vent filter membrane 34 functions to prevent liquid from passing upwardly. The vent filter membrane 34 functions with the sleeve 23 and the needle 33 to: a) Provide bidirectional gas flow from the vial headspace 20 to a pressure sensor 36 located in an electronic unit 38 during measurement or to the ambient during the initial or the final venting stages; and b) To prevent any liquid flow from the vial 10 to the pressure sensor 36 or to ambient in order to protect the operator from bacterial or viral contamination.

The fitment 22, including needle 33, forms an integral disposal unit that can be placed on the upper end of a container 10. The fitment 22 is adapted to receive a tubular projection 40 of the removable electronic sensor unit 38 so that the projection is sealingly engaged, such as by a seal ring 41, with top section 27 of the integral tubular portion 26.

The electronic unit 38 includes pressure sensor 36 and is preferably connected to remote electronics (not shown), as described in U.S. Pat. No. 5,232,839 which is incorporated in its entirety into the present invention. In addition, the electronic unit 38 includes a bottle in place sensor 42 and a positivity light 44.

The presence of organisms in a specimen can be detected by a microprocessor (not shown), incorporated in the remote electronics, which employs a number of pre-set criteria based upon the dynamic characteristics of the absolute value of the rates of change of pressure. These rates generally depend upon the following parameters: a) Type of organism (aerobic or anaerobic); b) Media/Temperature combination (intrinsic properties); c) Total volume of medium; d) Volume of the bottle's headspace; and e) Pneumatic and electrical variations among components.

These parameters affect the general trend of the rates of change. The microprocessor incorporates a plurality of algorithms that function to recognize the relatively wide range of absolute value of the rates and detect microorganisms by their rates of growth. The algorithms, however, do not consider the pressure values and do not make a comparison of these values to a known sample.

After the sample is placed in the container 10 through a hypodermic needle (not shown), the disposable fitment 22 is placed on top of the container 10. The fitment 22 is pressed downwardly so that the hypodermic needle 33 penetrates the stopper 14 and the lower end of the sleeve 24 engages the shoulder 18. In this position, the free end of needle 33 is in the headspace 20 above the level of the liquid medium 21. The electronic unit 38 is then inserted into the disposable fitment 22.

After a predetermined amount of time, a pressure magnitude is read by the pressure sensor 36, processed by the signal processor and stored in the memory of the microprocessor as a first value or data point. The initial activation time allows the container 10, which is placed in an incubator (not shown) to reach its incubation temperature.

The procedure repeats itself at the predetermined time intervals. The algorithms embedded in the microprocessor determines whether significant pressure rate change has occurred due to presence of organisms. If a positive decision is made, the microprocessor (not shown) activates the visual indicator, such as a positivity light 44. Indicator light 44 will stay on, regardless of any pressure variations, until the reset switch is pressed again to start a new test.

FIG. 2 illustrates a typical voltage-time curve generated by a pressure sensor measuring the developed pressure at the vial's headspace. In this example, the typical pressure analysis of a mixture of a culture broth and reagents leads to a significant drift where after about 50 days, the baseline drift is +30 millivolts to −15 millivolts (a change of 45 millivolts).

By comparison, in FIG. 3, the graph shows the curve of voltage versus time in a typical pressure analysis of the identical mixture of culture broth and reagents as shown in the curve of FIG. 2 but with the addition of a pair of poising agents added to the mixture in accordance with the present invention. In this example of a typical pressure analysis of a mixture of a culture broth and reagents, the addition of a pair of poising agents leads to a less significant drift. The baseline drift after 50 days is +30 to +15 millivolts (a change of 15 millivolts).

Referring to FIG. 4, there is a graph showing the curve of voltage versus time in a typical pressure analysis of the identical mixture of culture broth and reagents plus a sample to be tested to determine the presence of an organism. In this example of a typical pressure analysis of a mixture of a culture broth and reagents and a pair of poising agents, one of the algorithms is satisfied because of the significant decrease in headspace pressure, which is the result of oxygen consumption by the organism.

Referring to FIG. 5, there are two sets of examples from two different herds, each of 100 animals. Using the prior art, typical pressure analysis of a mixture of a culture broth and reagents and a sample from each animal, the percentage of false positives for the first herd was 27.14% and for the second herd was 6.33%, where there was actually no organism. The samples that were mixed with the culture broth and reagents and placed into the bottle were processed fecal samples that may contain "mycobacterium paratuberculosis." Using the pressure analysis of a mixture of a culture broth and reagents and two poising agents, in accordance with the present invention, and a sample from each animal, the percentage of false positives for the first herd was reduced to 5.71%, and for the second herd was reduced to 0.00%, where there actually was no organism.

Referring to FIG. 6, there is shown the recovery of true positives from the two sets of examples from the first herd of animals. In the first herd indicated on the left, using the prior art, typical pressure analysis of a mixture of a culture broth and reagents and a sample from each animal, the percentage of true positives is 21.43%. The percentage of true positives for these animals same animals indicated on the right side of the chart, using the pressure analysis of a mixture of a culture broth and reagents and two poising agents, in accordance with the present invention, and a sample from each animal, the percentage of true positives is higher or 38.57%.

While only one sample container 10 is shown, the system typically monitors a plurality of sample containers 10. Typically, a plurality of sample bottles are placed in an incubator. The location of each bottle can be recognized by the bottle in place sensor 42. The bottles 10 can be incubated for a long period of time, including but not limited to 3 or 4 months. The bottles are automatically monitored, as discussed before. An operator can visually determine when a positive has been sensed in a bottle when the light 44 turns on.

While one embodiment of the invention has been described above, it is within the terms of the present invention to add the poising agents of the present invention to any liquid mixture which is being monitored using a redox sensor so as to reduce the background noise due to undefined chemical reactions within the system and thereby significantly reduce false positives.

In another embodiment, the poising agents of the present can be added to any liquid mixture which is being monitored using a redox sensor, such as a calorimetric or fluorimetric redox sensor, so as to reduce the background noise due to undefined chemical reactions within the calorimetric dye or fluorimetric dye, respectively, and thereby significantly reduce false positives. Using these sensors, oxygen attaches to the calorimetric dye or fluorimetric dye. In these embodiments, as with the embodiment described before, there can be a problem of false positives due to chemical redox reactions (reduction/oxidation). Examples of fluorimetric dyes are tris-4,7-diphenyl-1,10-phenanthroline ruthenium (II) salt; tris-2,2'-bipyridyl ruthenium (II) salt; and 9,10-diphenyl anthracene. Examples of colorimetric dyes are resazurin and tetrazolium dyes, for example MTT (3-4,5-dimethylthiazol-2,5-diphenyltetrazolium bromide). Examples of a luminescent dyes include luminescent sensor compounds selected from the group comprising platinum (II); palladium (II) octaethyl complexes immobilized in PMMA (polymethyl methacrylate); CAB (Cellulose acetate brityrate); platinum (II) and palladium (II) octaethyl porphrin keytone complexes immobilized in PVC and polystyrene. The colorimetric dye or fluorimetric dye can react with oxygen from the reagents themselves, such as the growth supplement and/or the antibiotic supplement, even without a sample being added to the culture mixture in a container. The result is that the color of the colorimetric dye changes or the fluorimetric dye doesn't fluoresce. In other words, there is a signal generated by the utilization or consumption of oxygen within the system due to reagent-driven chemical reactions (baseline drift) that will, in turn, cause increased numbers of false positives. This baseline drift, also referred to as background noise, cannot be predicted because the reagents are not chemically defined and are comprised of variable amounts of reactive components. Thus, it is within the terms of the present invention to add the poising agents of the present invention to any liquid mixture which is being monitored using a colorimetric or fluorimetric redox sensor so as to reduce the background noise due to undefined chemical reactions within the system and thereby significantly reduce false positives.

In this connection, it will be appreciated that the test procedure of the present invention is qualitative—i.e., presence of a microorganism is determined but no effort is made to establish concentration. In the same way, no effort is made to establish either the family or type of microorganism. These determinations can be made in other procedures, if desired. The present invention seeks merely to determine presence of a microorganism, regardless of type or concentrations. Thereby, the present invention may be applied to kinetic or threshold end point determinations.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

We claim:

1. A method of stabilizing the output signal of a system that detects microbiological growth in a sealed sample container that contains a sample which may contain an unknown microorganism, the method comprising the steps of;
   (a) providing a sealed sample container which contains a fluid mixture of a culture broth, the sample, and at least one poising agent for stabilizing baseline pressure within a headspace above the fluid mixture in the sample container;
   (b) monitoring pressure changes within the headspace of the sealed sample container; and
   (c) indicating a presence of microbiological growth within the sealed sample container as a function of the change of the headspace pressure.

2. The method set forth in claim 1 wherein said step (a) comprises the step of providing a pair of coupled poising agents.

3. The method set forth in claim 2 wherein said pair of coupled poising agents are selected from the group consisting essentially of ferricyanide/ferrocyanide and ferrous/ferric.

4. The method set forth in claim 3 wherein said pair of coupled poising agents is ferricyanide/ferrocyanide.

5. The method set forth in claim 4 wherein the concentration of both components of ferricyanide/ferrocyanide is within the range of 0.00005M to 0.001M total concentration.

6. The method set forth in claim 5 wherein the ferricyanide/ferrocyanide ratio is between 1:4 to 4:1.

7. The method set forth in claim 2 including the step of providing a second poising agent which is a reversible oxidation-reduction indicator.

8. The method set forth in claim 7 including the step of providing a second poising agent selected from the group consisting essentially of methylene blue, toluidine blue, azure I, and gallocyanide.

9. The method set forth in claim 1 wherein the said step (a) further comprises the step of adding at least two reagent mixtures.

10. The method set forth in claim 9 wherein the said step (a) includes the step of adding at least one reagent mixture of a growth supplement and a second reagent mixture of an antibiotic supplement.

11. The method set forth in claim 7 wherein the said step (a) further comprises the step of adding at least two reagent mixtures.

12. The method set forth in claim 11 wherein the said step (a) includes the step of adding at least one reagent mixture of a growth supplement and a second reagent mixture of an antibiotic supplement.

* * * * *